United States Patent [19]

Williams

[11] Patent Number: 5,016,999
[45] Date of Patent: May 21, 1991

[54] DISCRETE LENS EYEGLASSES

[76] Inventor: Ronnie E. Williams, 352 Kilarney Dr., Durham, N.C. 27703

[21] Appl. No.: 427,573

[22] Filed: Oct. 27, 1989

[51] Int. Cl.$^5$ ............................................. G02C 7/04
[52] U.S. Cl. ........................................ 351/41; 351/159
[58] Field of Search ...................... 351/41, 47, 57, 154, 351/86, 159, 161

[56] References Cited
U.S. PATENT DOCUMENTS
3,591,264  7/1971  Forrest ........................... 351/161 X OTHER PUBLICATIONS
Press-on Optics, Mentor, Journal of the American Optometric Assoc., 4/76.

Primary Examiner—Rodney B. Bovernick
Attorney, Agent, or Firm—Robert M. Wolters

[57] ABSTRACT

A discrete lens eyeglass is provided to be worn against the face in front of and spaced from the eye of the wearer. The eyeglass comprises a shallow concave-convex lens body which is worn convex toward the eye. There is an integral rearwardly projecting peripheral flange on the lens body which substantially engages the skin of the face. A foam cushioning material is provided on the edge of the flange for a comfortable fit with the face, and adhesive is applied to the foam for securing the eyeglass to the face.

5 Claims, 1 Drawing Sheet

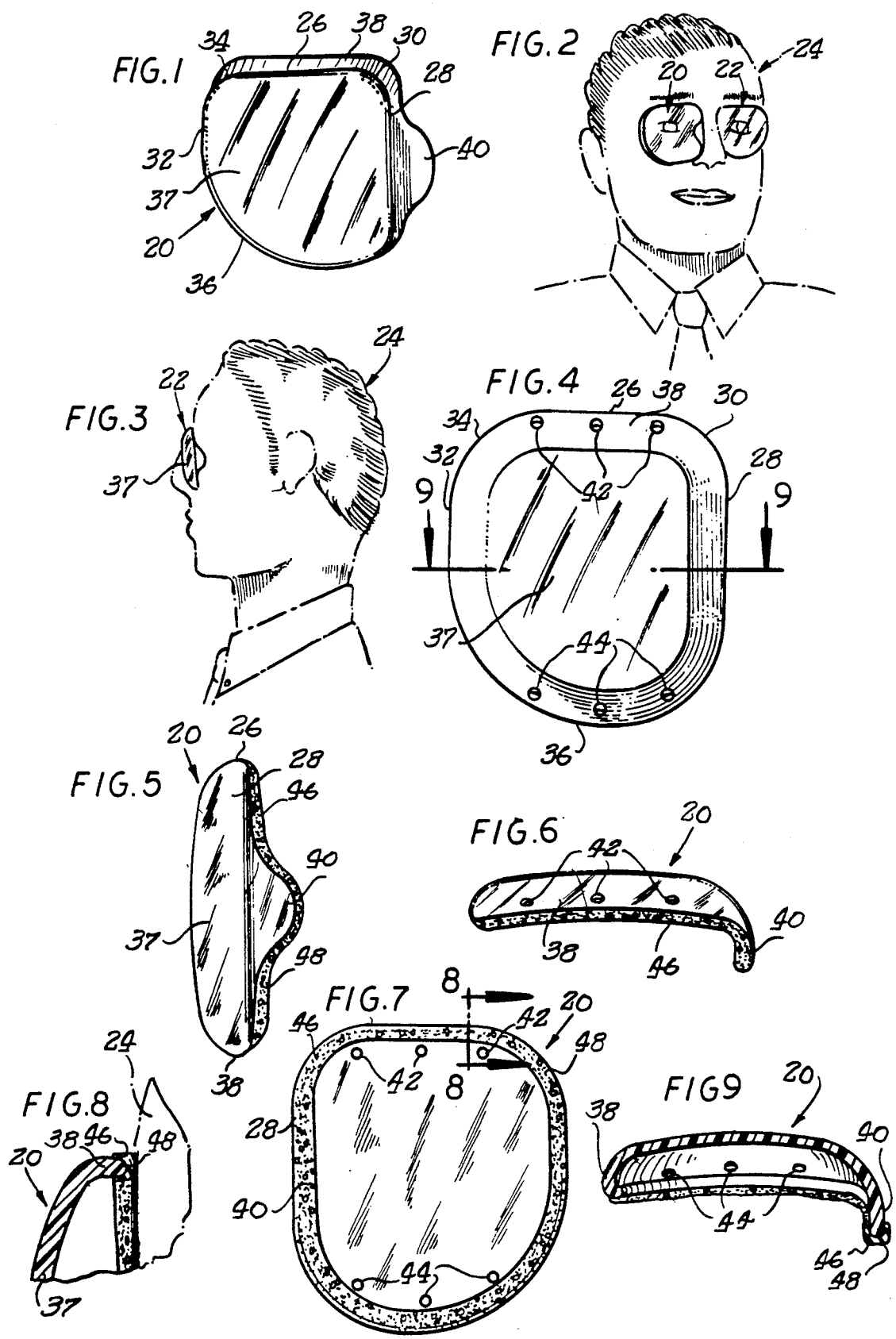

DISCRETE LENS EYEGLASSES

BACKGROUND OF THE INVENTION

Eyeglasses are widely used both to protect the eyes, and to improve vision. The present invention is concerned primarily with safety glasses for protecting the eyes, but the principles are equally applicable to prescription corrective lenses, and also to sunglasses.

Prior art eyeglasses are generally one of two types. One type has lenses supported by a frame with the lenses positioned forwardly of the eyes. These are disadvantageous in that there is pressure on the bridge of the nose, and tension behind the ears from the temple pieces. The second type of prior art eyeglasses comprises contact lenses which are worn directly on the eye in front of the eye lens, and at least in part in contact with the cornea. Many people cannot tolerate contact lenses, and they are available only on prescription. Furthermore, they are of limited use in protecting the eye, and could not generally be classified as safety glasses.

Safety glasses in the past have thus been restricted to lenses mounted in frame and carried in front of the face. These do generally provide satisfactory protection for the eyes, but as indicated may be physically uncomfortable. Futhermore, since they project forwardly of the face, they are in a position where they can be contacted readily by work pieces or the like, thereby being pushed against the nose of the wearer and possibly causing damage thereto, and also bending the frames. There are certain uses of protective glasses, such as working under automobiles, for example, where there is very little room for eye lenses and frames that project forwardly of the face.

OBJECT AND SUMMARY OF THE PRESENT INVENTION

It is an object of the present invention to provide safety eyeglasses comprising discrete lenses which are worn directly on the face and in front of and spaced from the eyes.

More particularly, it is an object of the present invention to provide discrete lens eyeglasses which are formed of a tough and resilient resinous plastic material which are shaped to engage the face in the vicinity of the eyes and which are peripherally padded with a foam rubber or plastic for cushioned comfort on the face, and which are adhesively adhered to the skin.

In accordance with the present invention a pair of eye lenses are provided which are essentially mirror images of one another. Each approximates a circle of about three inches in diameter and is provided with foam rubber or plastic about the outer edge thereof for cushioning against the face. A suitable adhesive is provided on the foam material to adhere to the face without injury or irritation thereto. The lenses can readily be dyed or otherwise colored for protection of the eyes from the sun or other bright lights. If desired the lenses could also be ground to prescription as corrective eye lenses.

The Drawings

The present invention will best be understood from the following specification when studied with the accompanying drawings, wherein:

FIG. 1 is a front view of one lens constructed in accordance with the present invention;

FIG. 2 is a front perspective view of a pair of such lenses as applied to the face of a wearer;

FIG. 3 is a side view showing one of the lenses applied to the face of the wearer;

FIG. 4 is an enlarged front view of the same lens shown in FIG. 1;

FIG. 5 is a side view of the lens of FIG. 4;

FIG. 6 is a top view of the same lens;

FIG. 7 is a rear view of the lens;

FIG. 8 is a fragmentary view partially in section as taken along the line 8-8 on a larger scale, and particularly showing the adhesive for securing a lens to the skin of the user, and;

FIG. 9 is a view generally similar to FIG. 6, but taken as a section about at the horizontal mid portion of the lens, as indicated along the line 9—9 in FIG. 4.

Detailed Disclosure of the Illustrative Embodiment

Clear plastics are widely used at the present time in the construction of conventional eyeglass lenses. They are suscepticle to dyeing to provide sunglasses. They do not break as readily as glass lenses, and are not nearly so dangerous when they do suffer breakage of one sort or another. Many such glasses are made of an acrylic plastic. Other plastics that are suitable include methylmethacrylate, polycarbonate, polystyrene, and dried Sol-Gel glass. It is believed that there are other plastic materials that would also be suitable, but this provides a workable list.

In accordance with the present invention, at least one such clear plastic product it utilized to mold a lens 20 as shown in most of the figures of the present set of drawings, and specifically comprising a right eye lens. A mirror image left eye lens 22 is utilized simultaneously to protect both eyes of a wearer indicated at 24.

The lens is of concave-convex construction, being concave toward the face, and of rather shallow concavity. The lens includes a substantially straight. upper edge and a substantially straight side edge 28 adjacent the nose and joined by a rather short arc 30. A depending outer edge 32 also is substantially straight, and is joined to the top edge by a relatively short arc 34. The remainder of the periphery of the lens comprises a continuous curve 36 extending between the lower portions of the two side edges 28 and 32, both of which are substantially vertical as worn.

The front portion of the lens spaced inwardly from the periphery as just described is of a shallow concave-convex construction as previously indicated. The entire periphery of the lens is turned rearwardly as indicated at 38 to impinge against the face of the wearer. In addition, there is a protuberance 40 of smoothly rounded shape that extends inwardly adjacent the nose of the wearer for fitting against the side of the nose generally in the position usually occupied by the eyepiece of a conventional eyeglass frame. Ventilation holes 42 extend through the lens adjacent the upper portion thereof, and similar ventilation holes 44 extend through the lens adjacent the bottom portion thereof. These holes provide for ventilation to decrease perspiration within the lens, and in the case of the lower holes or openings 44, also to carry away sweat condensed vapor.

The entire plastic portion of the eyeglass lens has now been described. In addition to the plastic portion, there is a foam rubber or plastic edge portion 46 which lies along the edge or periphery of the lens as it extends rearwardly into proximity with the wearer's face. The foam rubber or plastic is provided as a channel or bead about the edge, and it may not extend over the protrusion 40. The foam 46 further is provided with a coating 48 of adhesive to secure the lens to the face of the wearer. The adhesive must be of a type that will not damage the skin, and need not be continuous along the foam material 46. It must not irritate the face, and it must also be readily removed therefrom when it is desired to remove the lenses. One known material that fits the requirements is called flexible collodion. It may be that two or three dabs of the material will be sufficient, rather than a continuous coating. There are doubtless other adhesives that would work equally well.

It is contemplated that there would be a variety of sizes of lens blanks made, due to the different facial structures of different individuals. It is anticipated that there would be three to five or more sets of lenses that would be conventionally injected molded. Finishing would be done at the site of sale, which would include grinding the edges of the lenses for a best fit with an individual wearer's face. The foam material then would be applied, preferably with an adhesive, to secure to the periphery of the lens. Two or three dabs or adhesive material, or perhaps even a continuous coating thereof, would be applied to the surface of the foam material to secure the lens in place on the wearer's face. As will be apparent, the lens conforms rather closely to the wearer's face, thus allowing better clearance in close quarters, such as working under an automobile, and avoiding contact with parts of the workpiece which could damage the lens or injure the wearer.

In addition to the foregoing, the lens could be dyed to form a sunglass type of lens, or it could be dyed a very deep color for use in welding. Furthermore, the lens could be prescription ground, if so desired. The specific example of the invention as herein shown and described is for illustrative purposes. Various changes in structure will no doubt occur to those skilled in the art, and will be understood as forming a part of the present invention insofaras they fall within the spirit and scope of the appended claims.

The invention is claimed as follows:

1. A discrete lens eyeglass for positioning against the face in front of and spaced from an eye, comprising a shallow concave-convex lens body of transparent plastic material to be worn rearwardly concave toward an eye, and an integral rearwardly projecting peripheral flange on said lens body for substantial engagement with the skin of a face in the vicinity of an eye, and means on said flange including adhesive means for securing said eyeglass to the skin of a face, and further including a protuberance on said flange for positioning alongside of the nose.

2. A discrete lens eyeglass as set forth in claim 1 wherein the means on said flange includes cushioning material with the adhesive on said cushioning material.

3. A discrete lens eyeglass for positioning against the face in front of and spaced from the eye, comprising a shallow concave-convex lens body of transparent plastic material of sufficient strength and rigidity for independent eyeglass existence to be worn rearwardly concave toward an eye, and an integral rearwardly projecting peripheral flange on said lens body for substantial engagement with the skin of a face in the vicinity of an eye, and means on said flange including adhesive means for securing said eyeglass to the skin of a face, said eyeglass inwardly of said flange being free of adhesive, said lens body having a top edge which is substantially straight and in an edge adjacent the nose which is substantially straight.

4. A discrete lens eyeglass as set forth in claim 3 and further including a bottom portion of said lens as a long curve extending from the straight edge adjacent the nose.

5. A discrete lens eyeglass for positioning against the face in front of and spaced from an eye, comprising a shallow concave-convex lens body of transparent plastic material to be worn rearwardly concave toward an eye, and an integral rearwardly projecting flange on said lens body for substantial engagement with the skin of a face in the vicinity of an eye, and means on said flange including adhesive means for securing said eyeglass to the skin of a face, and further including vent holes therein substantially adjacent the top and the bottom of the eyeglass.

* * * * *